| United States Patent [19] | [11] Patent Number: 4,708,944 |
| --- | --- |
| Someno et al. | [45] Date of Patent: Nov. 24, 1987 |

[54] PROTEASE ADSORBENT AND PROCESS FOR PURIFYING TPA UTILIZING THE SAME

[75] Inventors: Tetsuya Someno; Kazuo Kato; Yasushi Takahashi, all of Saitama; Shinichi Ishii, Hokkaido; Tomio Takeuchi; Hamao Umezawa, both of Tokyo, all of Japan

[73] Assignee: Nippon Kayaku Kabushiki Kaisha, Tokyo, Japan

[21] Appl. No.: 749,713

[22] Filed: Jun. 28, 1985

[30] Foreign Application Priority Data

Jul. 6, 1984 [JP] Japan ................................. 59-138924

[51] Int. Cl.$^4$ ............................................... B01J 37/36
[52] U.S. Cl. ......................................... 502/7; 530/331; 435/215
[58] Field of Search ..................... 502/7, 401, 402, 404

[56] References Cited

U.S. PATENT DOCUMENTS 3,947,352  3/1976  Cuatrecasas et al. ........... 502/404 X
4,525,465  6/1985  Someno et al. ......................... 502/7

FOREIGN PATENT DOCUMENTS 627783   1/1982  Switzerland .
1028679  6/1981  U.S.S.R. .............................. 502/404

OTHER PUBLICATIONS

Chemical Abstracts, vol. 96, 1982, p. 368, Abstract No. 138603n.
Chemical Abstracts, vol. 101, 1984, p. 704, Abstract No. 211729m.
Chemical Abstracts, vol. 93, 1980, p. 329, Abstract No. 109752t.
Biochimica Et Biophysica Acta, vol. 717, 1982, pp. 327–336.
FEBS Letters, vol. 146, No. 2, Sep. 1982, pp. 289–292.

*Primary Examiner*—Patrick P. Garvin
*Attorney, Agent, or Firm*—Henry C. Nields

[57] ABSTRACT

A protease adsorbent wherein valyl-glycyl-argininal is bound to a water-insoluble carrier and a process for purifying TPA utilizing the same.

4 Claims, No Drawings

PROTEASE ADSORBENT AND PROCESS FOR PURIFYING TPA UTILIZING THE SAME

BACKGROUND OF THE INVENTION

Recently processes for the purification of tissue plasminogen activator (hereinafter referred to as TPA) with the use of an adsorbent wherein a ligand having an affinity for TPA is attached to a water-insoluble carrier have been developed.

For example, fibrin/Sepharose (see Per Wallen et al., Biochimica Biophsica Acta, 719, 318-328, 1982) and concanavalin A/agarose (see Dingeman C. Rijken et al., The Journal of Biological Chemistry, 256, No. 1, 7035-7041, 1981) each prepared by adsorbing a substrate of TPA in vivo as a ligand by a carrier have been devloped. There have been further developed processes for the purification of TPA with polyclonal and monoclonal antibodies of TPA/Sepharose by taking advantage of the affinity of an antigen to an antibody (see P.A. Andreasen et al., The EMBO Journal, 3, No. 1, 51-56, 1984: and L.S. Nielsen et al., ibid, 2, No. 1, 115-119, 1983).

Furthermore there has been known a process for the purification of TPA with an affinity resin by using a low molecular weight compound as a ligand such as arginine/Sepharose (see M. Ronby et al., Febs Letters, 146, No. 2, 289-292, 1982). However this process suffers some disadvantages. That is, the affinity of the arginine/Sepharose to TPA is not so high that the purification of TPA from its crude solution might not be readily carried out. Therefore a pretreatment with chromatographic techniques is required. In addition, this process gives an insufficient yield.

SUMMARY OF THE INVENTION

As a result of our studies on the purification of TPA, we have found that an adsorbent wherein valyl-glycyl-argininal (hereinafter referred to as an argininal derivative) is employed as a ligand and bound to a water insoluble carrier would effectively adsorb TPA and readily desorb the same by simply adjusting the pH value thereof.

The present invention has been completed on the basis of the above findings.

DETAILED DESCRIPTION OF THE INVENTION

In the protease adsorbent of the present invention, an α-amino group of valine in the argininal derivative employed as a ligand is attached to a carrier. This argininal derivative may be readily synthesized in a large amount from commercially available L-leupeptin.

Examples of valyl-glycyl-argininal available as a ligand are D-valyl-glycyl-DL-argininal, L-valyl-glycyl-DL-argininal and DL-valyl-glycyl-DL-argininal.

The water-insoluble carrier used in the present invention is not particularly restricted and those having a functional group capable of attaching to the α-amino group of the argininal derivative may be employed without any limitation. Examples of these water-insoluble carriers are acidic ion exchange resins such as metacrylic acid/divinylbenzene copolymer, crosslinked polyacrylamide resins and high-molecular polysaccharides. Examples of the crosslinked polyacrylamide resins are Bio-Gel P ®, hydrazide Bio-Gel P ® and Bio-Gen CH ® (each mfd. by Bio-Rad Co., Ltd.). Examples of the high-molecular polysaccharides are agarose gels such as Sepharose 2B ®, Sepharose 4B ®, Sepharose 6B ® and CH-Sepharose 4B ® (each mfd. by Pharmacia AB), and Bio-Gel A ® (mfd. by Bio-Rad Co., Ltd.), crosslinked dextran gels such as Sephadex ® and CM-Sephadex ® (each mfg. by Phrmacia AB) and cellulose products such as Cellex ® and Cellex CM ® (each mfd. by Bio-Rad Co., Ltd.). Among these carriers, agarose gels and crosslinked dextran gels, in particular agarose gels, are preferable.

Examples of the functional group are hydroxyl group, carboxyl group and derivatives thereof. Examples of carriers having hydroxyl group(s) are Sepharose 2B ®, Sepharose 4B ®, Sepharose 6B ®, Bio-Gen A ®, Sephadex ® and Cellex ®. Examples of those having carboxyl group(s) are Bio-Gel CM ®, CH-Sepharose 4B ®, CM-Sephadex ® and Cellex CM ®. While examples of those having derivative(s) of carboxyl group are Bio-Gel P ® having a carbamoyl group and Hydrazide Bio-Gel P ® having a hydrazinocarbonyl group.

In order to prepare the adsorbent of the present invention, an argininal derivative having a protected aldehyde group is reacted with a water-insoluble carrier having an activated functional group as described above and subsequently the protective group for the aldehyde group is removed. Lower dialkyl acetals such as dibutyl acetal are preferable as the protective group for the aldehyde group.

When the functional group is a hydroxyl group, it may be activated by reacting with a cyanogen halide. While the functional group is a carboxyl group, it may be activated by conventional methods employed in regard to peptide, e.g. by activating esterification or with the use of an acid anhydride. It is preferable to activate said carboxyl group by using succinimide or a water-soluble carbodiimide.

The reaction between the argininal derivative having a protected aldehyde group and the activated water-insoluble carrier may be carried out, e.g., in the presence of a water soluble carbodiimide at a pH value of 3 to 7 (preferably 4 to 6) and at 25 to 45° C. (preferably at 35 to 40° C.) for 10 to 30 hours (preferably for 15 to 25 hours) in a solvent. Examples of the water-soluble carbodiimide are 1-ethyl-3-(3-dimethylaminopropyl)carbodiimide and 1-cyclohexyl-3-(2-morpholinoethyl)carbodiimide. The amount thereof may be 1 to 20 g (preferably 5 to 10 g) per 100 ml of the gelatinized water-insoluble carrier.

Examples of the solvent are 0 to 50 % solutions of dimethylformamide or dioxane each comprising a salt solution or a buffer solution capable of maintaining a pH value of 3 to 7.

There are some commercially available carriers having a functional group previously activated by succinimide or an epoxy group, e.g., Activated CH-Sepharose 4B ® and Epoxy-activated Sepharose 4B ®. In the case of these carriers, it is not necessary to reactivate the functional group and they may be reacted as such with the argininal derivative having a protected aldehyde group.

The protective group for the aldehyde group of the reaction product thus obtained may be removed by hydrolyzing the product in a buffer solution of pH 1 to 4 (preferably 2 to 3) at 20° to 50° C. (preferably at 30° to 45° C.) for 24 to 120 hours (preferably for 48 to 96 hours). Examples of the buffer solution used herein are those comprising mineral acids such as hydrochloric acid or phosphoric acid, organic acids such as tartaric acid, citric acid, lactic acid, succinic acid and acetic acid and/or sodium or potassium salts thereof.

In the adsorbent of the present invention thus obtained, 0.1 to 10 μM of the argininal derivative, which is a ligand, is bound to 1 ml of the water-insoluble carrier. In order to purify proteases, those wherein 0.5 to 5 μM of the argininal derivative is bound to 1 ml of the water-insoluble carrier is preferable.

The protease adsorbent thus prepared is available in purifying proteases, in particular TPA.

TPA may be purified by using the protease adsorbent of the present invention as follows.

The abovementioned adsorbent is immersed in a buffer solution of pH 5 to 10 (preferably 6 to 8), then packed into a column and thoroughly equilibrated with the same buffer solution as used above. In this step, buffer solutions available in a pH range of 5 to 10 may be used without any limitation. For example, those comprising sodium phosphate/phosphoric acid, potassium phosphate/phosphoric acid, sodium acetate/acetic acid and trishydroxymethylaminomethane/hydrochloric acid may be employed. The salt concentration of the buffer solution is not particularly restricted and preferably from 0.025 to 0.5 M.

Then a crude TPA solution adjusted to a pH value of 5 to 10 (preferably 6 to 8) is passed through said adsorbent column to thereby adsorb the TPA by the adsorbent. After washing the adsorbent retaining TPA with the same buffer solution as used above, the TPA was eluted with an aqueous solution of an acid, a solution of a water-soluble salt or a buffer solution each having a pH value of 1 to 4 (preferably 2 to 3) to give an aqueous solution of TPA of a higher purity. Examples of the acid solution are aqueous solutions of citric acid, tartaric acid, lactic acid, succinic acid, acetic acid, phophoric acid and hydrochloric acid. Examples of the solution of a water-soluble salt are aqueous solutions of sodium chloride/hydrochloric acid, potassium chloride/hydrochloric acid or sodium sulfate/sulfuric acid. While examples of the buffer solution are aqueous solutions of sodium phosphate/phosphoric acid, potassium phosphate/phosphoric acid, citric acid/sodium citrate and succinic acid/borax, lactic acid/sodium lactate, acetic acid/sodium acetate and tartaric acid/sodium tartrate.

Instead of the column manner as descirbed above, the process of the present invention may be carried out in a batch manner.

The argininal derivative having a protected aldehyde group used in the preparation of the adsorbent of the present invention may be prepared by the following methods. Leupeptin is converted into leupeptin dibutyl acetal by the process described in Japanese Patent Laid-Open No. 37185/1980. The obtained leupeptin dibutyl acetal is then reacted with pronase E to give argininal dibutyl acetal. The obtained product is condensed with N-protected glycine in a manner conventionally employed in regard of peptide, e.g.:
(1) acid halide method;
(2) activating esterification with N-hydroxysuccinimide, p-nitrophenol or pentachlorophenol;
(3) carbodiimide method with dicyclohexylcarbodiimide or dimethylaminopropylcarbodiimide;
(4) with the use of a condensation agent such as diphenyl phosphorazidate, N-ethoxycarbonyl-2-ethoxydihydroquinoline, N-ethyl-5-phenylisoxazolium 3'-sulfonate, or 6-chloro-1-p-chlorobenzenesulfonyloxybenzotriazole;
(5) with the use of a mixed anhydride such as ethyl chloroformate and isobutyl chloroformate; or
(6) azide method. Examples of the N-protective group as used herein are those removable by catalytic reduction or similar procedures, e.g. benzyloxycarbonyl group and p-methoxybenzyloxycarbonyl group. Any conventional solvent may be used in the above condensation.

After removing the N-protective group by catalytic reduction, the obtained glycyl-argininal dibutyl acetal and N-protected valine are treated in the same manner as described above to give N-protected valyl-glycyl-argininal dibutyl acetal. Subsequently the N-protective group is removed by catalytic reduction to give an argininal derivative having a protected aldehyde group.

The catalytic reduction may be carried out in a solvent such as methanol with palladium black or similar agents in a conventional manner. Hydrolysis may be carried out in a water-miscible solvent such as methanol, ethanol, acetone, acetonitrile, dimethylformamide, tetrahydrofuran or dioxane with an approximately 0.3 to 0.5 N mineral or organic acid such as citric acid or oxalic acid.

The affinity resin of the present invention is available in purifying any types of TPA such as those obtained by tissue culture, by genetic engineering or occurring in vital tissues. It exhibits a particularly excellent effect of purifying TPA derived from human melanoma cells.

To further illustrate the present invention, the following examples will be given.

In the following Examples, each Rf value in thin layer chromatography was determined by the use of a thin layer plate, Silica gel 60F254 plate of 0.25 mm in thickness (mfd. by Merck) and a mixture of n-butanol/butyl acetate/acetic acid/water (4:2:1:1) as a developing solvent.

Optical rotations were determined with a mercury lamp at 578 nm.

Each compound was identified by field desorption mass spectrometry.

Each TPA activity as shown in the following Examples was determined by measuring the Amidolytic activity with H-D-Ileu-Pro-Arg-p-nitroanilide No. S-2288 (mfd. by Kabi AB) and then converting the obtained value into biological unit (PU).

EXAMPLE 1

Preparation of D-valyl-glycyl-D,L-argininal/Sepharose (1) Preparation of N-benzyloxycarbonyl-glycyl-D,L-argininal dibutyl acetal 1 g of D,L-argininal dibutyl acetal was dissolved in 30 ml of N,N'-dimethylformamide and 434 μl of triethylamine was added thereto. Then 1.13 g of N-benzyloxycarbonylglycine N-hydroxysuccinimide ester was added thereto in five portions within two hours and the reaction mixture thus obtained was stirred at room temperature for 20 hours. After distilling off the solvent in vacuo, the residue was subjected to column chromatography with the use of a silica gel carrier and developed with a solvent mixture of butanol/butyl acetate/acetic acid/water (4:2:1:1; v/v). A fraction of Rf 0.6 and positive to Sakaguchi reagent was concentrated in vacuo to give 1.04 g of a powder.

Silica gel TLC: Rf 0.6 (developing solvent; see above) (α) 25/578 −3.0° (C=1.2, methanol).

(2) Preparation of glycyl-D,L-argininal dibutyl acetal 644 mg of the obtained N-benzyloxycarbonyl-glycyl-D,L-argininal dibutyl acetal was dissolved in 30 ml of methanol and subjected to catalytic reduction with palladium black for four hours. After the completion of the reaction, the palladium black was removed and the solvent was distilled off in vacuo to give 390 mg of glycyl-D,L-argininal dibutyl acetal in the form of a powder.

Silicagel TLC: Rf 0.2 (see above).

(3) Preparation of N-benzyloxycarbonyl-D-valine-glycyl-D, L-argininal dibutyl acetal 380 mg of the glycyl-D,L-argininal dibutyl acetal thus obtained was dissolved in 10 ml of N,N'-dimethylformamide and 140 μl of triethylamine was added thereto. Then 418 mg of N-benzyloxycarbonyl-D-valine N-hydroxysuccinimide ester was added thereto in five portions within two hours. The obtained reaction mixture was stirred at room temperature for 20 hours. After distilling off the solvent in vacuo, the mixture was subjected to column chromatography with the use of silica gel as a carrier and the same developing solvent as described above. A fraction of Rf 0.7 and positive to Sakaguchi reagent was concentrated in vacuo to give 212 mg of a powder. (α)25/578 0° (C=0.7, acetic acid) FD-MS:m/z=579 (M+H)+.

(4) Preparation of D-valyl-glycyl-D,L-argininal dibutyl acetal 132 mg of the N-benzyloxycarbonyl-D-valyl-glycyl-D,L-argininal dibutyl acetal was dissolved in 10 ml of methanol and subjected to catalytic reduction with palladium black for four hours. After the completion of the reaction, the palladium black was removed and the solvent was distilled off in vacuo to give 138 mg of D-valyl-glycyl-D,L-argininal dibutyl acetal in the form of a powder.

(α)25/578 −3.9° (C=1.5, methanol).

(5) Preparation of D-valyl-glycyl-D,L-argininal/Sepharose 100 mg of the powder thus obtained was suspended in a mixture of 100 ml of an aqueous solution of morpholinoethansulfonic acid and 100 ml of dioxane and the obtained suspension was added to 70 ml of CH-Sepharose 4B ® (mfd. by Pharmacia AB) followed by adjusting the pH value of the mixture to 5. Then the mixture was stirred on a water bath at 37° C. and 3 g of carbodiimide was added thereto in in five portions within two hours. Stirring was continued for additional 20 hours. The resin was poured onto a glass filter, thoroughly washed with water and immersed in 300 ml of an aqueous solution of 0.2 M sodium citrate (pH 2.5) at 40° C. for 60 hours. After removing the buffer and washing with water, 70 ml of the title resin wherein 2.25M of the argininal derivative was attached to 1 ml of the carrier was obtained.

EXAMPLE 2

Preparation of L-valyl-glycyl-D,L-argininal/Sepharose 381 mg of glycyl-D,L-argininal dibutyl acetal, 417 mg of N-bynzyloxycarbonyl-L-valine N-hydroxysuccinimide ester and 150 μl of triethylamine were allowed to react in 10 ml of N,N'-dimethylformaide similar to Example 1. After teating the reaction mixture in the same manner as described in Example 1, 199 mg of N-benzyloxycarbonyl-L-valyl-glycyl-D,L-argininal dibutyl acetal was obtained in the form of a powder.

Silica gel TLC; Rf 0.7 (see above) (α)25/578 −3.9° (C=1.4, methanol).

The obtained powder was subjected to catalytic reduction in the same manner as described in Example 1 to give 115 mg of L-valyl-glycyl-D,L-argininal dibutyl acetal.

100 mg of the powder thus obtained was treated in the same manner as described in Example 1 to give 70 ml of the title resin wherein 315 μM of carrier of the argininal derivative was attached to 1 ml of the carrier.

EXAMPLE 3

1 ml of the TPA adsorbent prepared in Example 1 was packed into a column and thoroughly equilibrated with a 0.05 M sodium phosphate buffer solution (pH 7.0) containing 2% of common salt. Subsequently a 704 U/ml TPA solution was passed through the column to thereby adsorb TPA by the adsorbent. After washing the column with the same buffer solution as described above, the TPA adsorbed by the column was desorbed by using a 0.2 M citric acid solution to give 500 U of purified TPA in a yield of 71%. The specific activity of the obtained product was 55 times as high as that of the crude TPA.

EXAMPLE 4

The TPA affinity adsorbent prepared in Example 2 was suspended into a 0.1 M phosphate buffer solution containing 0.5% of common salt and 0.01% of Tween 80 and 10 ml of the adsorbent was packed into a column (ϕ1.1 cm×11 cm) and thoroughly equilibrated with the same buffer solution as described above. Then a crude TPA solution (specific activity:662 PU/mg protein, 79000 PU) was passed through the adsorbent at a flow rate of 7.2 ml/hour. After successively washing with the equilibrating buffer solution and a buffer solution of the same composition except that the table salt concentration was raised to 3%, the TPA was eluted with a 0.2 M aqueous solution of citric acid. Prior to the elution, 0.5 ml of 1 M tris-HCl (pH 9.0) was introduced into each test tube to thereby adjust the pH value of each TPA fraction around neutrality. The specific activity of the TPA thus eluted in a yield of 74% was 99700 PU/mg protein and was 134 times as high as that of the crude TPA. It was confirmed that the purified TPA was a single protein in SDS-polyacrylamide gel (12.5% gel) electrophoresis containing no reductant by Coomassie Brilliant Blue staining.

EXAMPLE 5

A crude solution of TPA (specific activity; 663 PU/mg protein, total activity; 80000 PU) was purified in the same manner as described in Example 3 with the use of D-valyl-glycyl-D,L-argininal/Sepharose prepared in the same manner as described in Examples 1 and 2.

The purified TPA thus eluted in a yield of 73% exhibited a specific activity of 90168 PU/mg protein and was a single protein in the same electrophoresis as described in Example 4.

REFERENTIAL EXAMPLE

Preparation of D,L-argininal dibutyl acetal hydrochloride 25 g of leupeptin dibutyl acetal hydrochloride prepared in the manner described in Japanese Patent Laid-Open No. 37185/1980 was suspended into 1000 ml of a 0.1 M N-ethylmorpholine hydrochloride buffer solution (pH 8.0) containing 0.02 M calcium chloride and 0.02 M manganese chloride. 1.25 g of pronase E was added thereto and the reaction mixture was stirred at 37° C. for 72 hours. Then the reaction mixture was passed through 500 ml of Diaion pH 20, washed with water and eluted with ethanol. Fractions positive to Sakaguchi reagent were combined to give 4.8 g of argininal dibutyl acetal hydrochloride.

($\alpha$) 25/578 + 0.5° (C=0.8, acetic acid)

m.p.: 164° to 166° C.

FD-MS: 289 (M +H)

What is claimed is:

1. A tissue plasminogen activator adsorbent wherein valyl-glycyl-argininal is bound to a water-insoluble carrier.

2. An adsordent as set forth in claim 1, wherein 0.1 to 10 $\mu$M of said valyl-glycyl-argininal is bound to 1 ml of said carrier.

3. An adsorbent as set forth in claim 1, wherein 0.5 to 5 $\mu$M of said valyl-glycyl-argininal is bound to 1 ml of said carrier.

4. An adsorbent as set forth in claim 1, wherein said carrier is agarose gel or crosslinked dextran gel.

* * * * *